United States Patent [19]

Aizawa et al.

[11] Patent Number: 5,308,861
[45] Date of Patent: May 3, 1994

[54] THERAPEUTIC AGENT FOR TREATING ATHEROSCLEROSIS OF MAMMALS

[75] Inventors: Katsuo Aizawa, Yokohama; Yukari Kuroiwa, Urawa, both of Japan

[73] Assignee: Nippon Petrochemicals Company, Limited, Tokyo, Japan

[21] Appl. No.: 875,367

[22] Filed: Apr. 29, 1992

[30] Foreign Application Priority Data

Apr. 30, 1991 [JP] Japan .................................. 3-126608

[51] Int. Cl.⁵ .............................................. A61K 31/40
[52] U.S. Cl. ...................................... 514/410; 514/824
[58] Field of Search .................................. 514/410, 824

[56] References Cited

U.S. PATENT DOCUMENTS

| | | | |
|---|---|---|---|
| 4,656,186 | 4/1987 | Bommer et al. | 514/410 |
| 4,675,338 | 6/1987 | Bommer et al. | 514/410 |
| 4,693,885 | 9/1987 | Bommer et al. | 424/2 |
| 4,886,831 | 12/1989 | Morcos et al. | 514/456 |
| 4,977,177 | 12/1990 | Bommer et al. | 514/410 |
| 4,997,639 | 3/1991 | Aizawa et al. | 424/9 |
| 5,004,811 | 4/1991 | Bommer et al. | 540/145 |
| 5,066,274 | 11/1991 | Bommer et al. | 604/20 |

OTHER PUBLICATIONS

F. Litvack, M.D., et al. (1985) Effects of Hematoporphyrin Derivative and Photodynamic Therapy on Atherosclerotic Rabbits, The American Journal of Cardiology 56:667–671.

V. Neave, M.D., et al. (1988) Hematoporphyrin Uptake in Atherosclerotic Plaques: Therapeutic Potentials, Neurosurgery 23:307–312.

*Primary Examiner*—Frederick E. Waddell
*Assistant Examiner*—Kimberly R. Jordan
*Attorney, Agent, or Firm*—Scully, Scott, Murphy & Presser

[57] ABSTRACT

A therapeutic agent used for photodynamic therapy of atherosclerosis of mammals, which agent comprises at least one member of fluorescent compounds selected from the group consisting of tetrapyrrole carboxylic acids having at least one carboxyl group, corresponding di- or tetrahydrotetrapyrrole carboxylic acids, and mono-, di- or polyamides of the tetrapyrrole carboxylic acids with amino-mono- or dicarboxylic acids and their salts.

13 Claims, No Drawings

THERAPEUTIC AGENT FOR TREATING ATHEROSCLEROSIS OF MAMMALS

BACKGROUND OF THE INVENTION (1) Field of the Invention

This invention relates to a therapeutic agent for photodynamic therapy of the atherosclerosis of animals, especially of mammals. More particularly, the invention relates to specific fluorescent compounds having a tetrapyrrole skeletal structure. An effective quantity of the compound is administered to a host and light rays of necessary wavelength are applied to the area of atherosclerosis to be treated, thereby regressing the atherosclerotic lesion by the cytotoxic singlet oxygen produced by the compound which is photodynamically excited.

(2) Description of the Prior Art

Atherosclerosis is a general term for local diseases of arteries, in which the functions of arteries are depressed by the intimal thickening, hardening and reconstruction of arterial walls. Included in these diseases are coronary atherosclerosis inducing myocardial infarction and angina pectoris, atherosclerosis obliterating in peripheral artery and abdominal aorta, and cerebral atherosclerosis inducing transient cerebral ischemia and cerebral infarction. As referred to above, the atherosclerosis is quite a serious condition as a fatal disease inducing myocardial infarction, angina pectoris, cerebral apoplexy or the like.

At present, there are two approaches for treating the atherosclerosis. One of them is surgical treatment in which the portion affected by atherosclerosis is directly treated. The other measure is medical treatment in which etiological factors relating to the occurrence and aggravation of the symptom of atherosclerosis is remedied. The medical treatment is mainly adopted presently for preventing the worsening and the occurrence of terminal complication by total amelioration of undesirable factors with alimentotherapy, exercise cure and pharmacological treatment. Meanwhile, there are few potential agents and curative means for direct treatment of atherosclerosis.

In the ordinary diagnosis of atherosclerosis, morbid parts in respective internal organs are mainly detected. Meanwhile, there are few methods for the diagnosis of artery system, the early detection of atherosclerotic portion and their quantitative evaluation.

There is hitherto known a method of diagnosis and therapy of atherosclerosis by administering a hematoporphyrin derivative to hypercholesterolemia rabbits and applying light rays. A typical hematoporphyrin derivative is exemplified by Photofrin II, which is described in THE AMERICAN JOURNAL OF CARDIOLOGY, 56, pp 667-671, 1985 "Effect of Hematoporphyrin Derivative and Photodynamic Therapy on Atherosclerotic Rabbits".

However, it was clarified by experiments of the present inventors that, when Photofrin II is used, it cannot be caused to accumulated selectively in the atherosclerotic lesion and marked therapeutic effect cannot be expected.

Incidentally, the compounds themselves in the present invention are already known as photodynamic diagnostic and photodynamic therapeutic agents for cancer which are described in U.S. Pat. Nos. 4,693,885; 4,656,186; 4,675,338; and 4,977,177 and European Laid-Open Patent No. 210351. It should be noted, however, that the field of art in the present invention is of course different from the field of art in the diagnosis and the therapy of cancer.

BRIEF SUMMARY OF THE INVENTION

It is, the object of the present invention to provide a therapeutic agent for photodynamic therapy which is applied directly (locally) to the morbid portions of atherosclerosis, thereby attaining a high therapeutic effect, which has been unsatisfactory in the conventional treating art for atherosclerosis.

In view of the above object, the present inventors have carried out extensive investigations and, as a result, they have found out a novel series of medicines effectively used in the photodynamic therapy of atherosclerosis.

The present invention provides a therapeutic agent for treating atherosclerosis of mammals, which agent comprises at least one member of fluorescent compounds selected from the group consisting of tetrapyrrole carboxylic acids having at least one carboxyl group represented by the following general formula, and corresponding di- or tetrahydrotetrapyrrole carboxylic acids, and mono-, di- and polyamides of said tetrapyrrole carboxylic acids with amino-mono- or dicarboyxlic acids, and their salts.

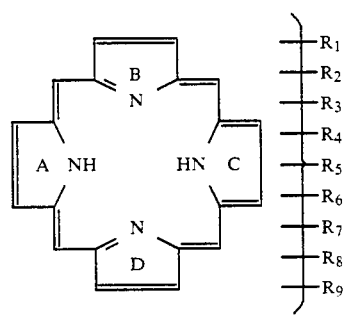

In the formula, $R_1$ is methyl,

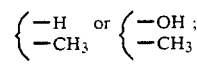

$R_2$ is H, vinyl, ethyl,

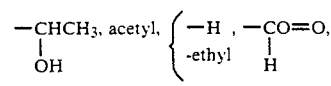

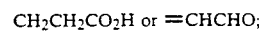

$R_3$ is methyl,

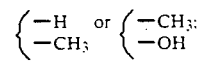

$R_4$ is H, vinyl, ethyl,

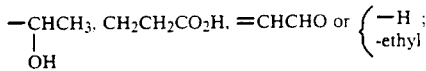

$R_5$ is methyl;
$R_6$ is H, $CH_2CH_2CO_2H$, $CH_2CH_2CO_2R$ or $CO_2H$;
$R_7$ is $CH_2CH_2CO_2H$, $CH_2CH_2CO_2R$ or

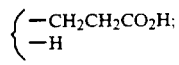

$R_8$ is methyl or

$R_9$ is H, COOH, $CH_2COOH$ or methyl; provided that when $R_1$, $R_2$, $R_3$, $R_4$, $R_7$ and $R_8$ represent two substituents or are divalent and attached to the same carbon, the respective pyrrole ring to which attached is a dihydropyrrole;
R is lower alkyl or benzyl;
$R_6$ and $R_9$, taken together are

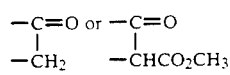

with the proviso that at least one of $R_1$ to $R_9$ is a free carboxyl group.

DETAILED DESCRIPTION OF THE INVENTION

All the compounds used in the present invention are fluorescent compounds, which are represented by the foregoing general formula. The tetrapyrrole carboxylic acid has at least one and preferably three carboxyl groups and it is desirable that the carboxyl groups are connected asymmetrically. For example, the carboxylic acid groups are present on the rings A and B side of the molecule or on the rings D and C side of the molecule. Also included in the compounds of the present invention are di- and tetrahydrotetrapyrrole carboxylic acids which correspond to the above tetrapyrrole. Furthermore, pharmaceutically acceptable salts of the carboxyl groups of these carboxylic acids such as salts of alkali metals, alkaline earth metals, ammonium and amines are included.

Furthermore, the compounds used in the present invention are mono-, di- and polyamides of amino monocarboxylic acid with the above tetrapyrrole carboxylic acids. Another usable groups of compounds are mono-, di- and polyamides of amino dicarboxylic acid with the same tetrapyrrole carboxylic acids as above. Further, pharmaceutically acceptable salts of the carboxyl groups of these mono-, di or polyamides such as the salts of alkali metals, alkaline earth metals, ammonium and amines are included.

The above amino monocarboxylic acids which forms mono-, di- or polyamide by connecting with the above tetrapyrrole carboxylic acid by way of polypeptide bonds are exemplified by serine, glycine, α-aminoalanine, β-aminoalanine, ε-amino-n-caproic acid, piperidine-2-carboxylic acid, piperidine-6-carboxylic acid, pyrrole-2-carboxylic acid, piperidine-6-propionic acid, pyrrole-5-acetic acid, and similar such acids. The preferred amino monocarboxylic acids are naturally occurring α-amino monocarboxylic acids, e.g., serine, alanine and glycine, which are readily available and provide the best results.

Exemplar amino dicarboxylic acids are α-aminosuccinic acid (aspartic acid), α-aminoglutaric acid (glutamic acid), β-aminoglutaric acid, β-aminosebacic acid, 2,6-piperidine dicarboxylic acid, 2,5-pyrrole dicarboxylic acid, 2-carboxypyrrole-5-acetic acid, 2-carboxypiperidine-6-propionic acid, α-aminoadipic acid, and α-aminoazelaic acid. The preferred amino dicarboxylic acids are the naturally occurring α-amino dicarboxylic acids such as aspartic acid and glutamic acid. These compounds are easily available and produce best results.

The especially preferable tetrapyrrole compounds used in the present invention are represented by the following general formula.

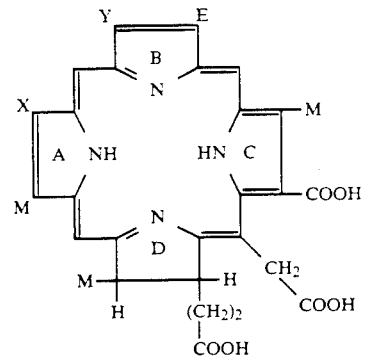

wherein, X is H, vinyl, ethyl, acetyl or formyl; Y is methyl or formyl; M is methyl; and E is ethyl.

Typical compounds of the tetrapyrrole classes are shown in Tables 1 and 2 in which the numbered positions of the tetrapyrrole ring structure are used to designate the position of the indicated substituent. The absence of double bonds in the ring system is designated under "dihydro" with each set of numbers (ring position) indicating the absence of a double bond between designated positions.

TABLE 1

| | Ring Position | | | | | | | | | |
|---|---|---|---|---|---|---|---|---|---|---|
| | A | | B | | C | | D | | | |
| Porphyrin | 1 | 2 | 6 | 7 | 11 | 12 | 14 | 16 | 17 | Dihydro |
| Coproporphyrin III | Me | Pr | Me | Pr | Me | Pr | H | Pr | Me | — |
| Deuteroporphyrin IX | Me | H | Me | H | Me | Pr | H | Pr | Me | — |
| Hematoporphyrin IX | Me | Me-CH-OH | Me | Me-CH-OH | Me | Pr | H | Pr | Me | — |

TABLE 1-continued

| Porphyrin | Ring Position | | | | | | | | | |
|---|---|---|---|---|---|---|---|---|---|---|
| | A | | B | | C | | D | | | |
| | 1 | 2 | 6 | 7 | 11 | 12 | 14 | 16 | 17 | Dihydro |
| Protoporphyrin IX | Me | V | Me | V | Me | Pr | H | Pr | Me | — |
| Photoprotoporphyrin IX (one of two isomers shown) | Me | V | { —Me / —OH | =CHCHO | Me | Pr | H | Pr | Me | 6,7 |
| Mesoporphyrin IX | Me | Et | Me | Et | Me | Pr | H | Pr | Me | — |
| Transmesochlorin IX | { Me / H | { Et / H | Me | Et | Me | Pr | H | Pr | Me | 1,2 |
| Transmesochlorin IX | Me | Et | { H / Me | { H / Et | Me | Pr | H | Pr | Me | 6,7 |
| Chlorin $e_4$ | Me | V | Me | Et | Me | $CO_2H$ | Me | { H / Pr | { H / Me | 16,17 |
| Chlorin $e_6$ | Me | V | Me | Et | Me | $CO_2H$ | Ac | { H / Pr | { H / Me | 16,17 |
| Mesochlorin $e_4$ | Me | Et | Me | Et | Me | $CO_2H$ | Me | { H / Pr | { H / Me | 16,17 |
| Isochlorin $e_4$ | Me | V | Me | Et | Me | H | Ac | { H / Pr | { H / Me | 16,17 |

TABLE 2

| Porphyrin | Ring Position | | | | | | | | | |
|---|---|---|---|---|---|---|---|---|---|---|
| | A | | B | | C | | | D | | |
| | 1 | 2 | 6 | 7 | 11 | 12 | 14 | 16 | 17 | Dihydro |
| Mesoisochlorin $e_4$ | Me | Et | Me | Et | Me | H | Ac | { H / Pr | { H / Me | 16,17 |
| Mesochlorin $e_6$ | Me | Et | Me | Et | Me | $CO_2H$ | Ac | { H / Pr | { H / Me | 16,17 |
| Bacteriochlorin $e_6$ | Me | ACL | { H / Me | { H / Et | Me | $CO_2H$ | Ac | { H / Pr | { H / Me | 6,7 / 16,17 |
| Bacteriochlorin $e_4$ | Me | ACL | { H / Me | { H / Et | Me | $CO_2H$ | Me | { H / Pr | { H / Me | 6,7 / 16,17 |
| Bacterioisochlorin $e_4$ | Me | ACL | { H / Me | { H / Et | Me | H | Ac | { H / Pr | { H / Me | 6,7 / 16,17 |
| 2-Desvinylchlorin $e_6$ (or Deuterochlorin $e_6$) | Me | H | Me | Et | Me | $CO_2H$ | Ac | { H / Pr | { H / Me | 16,17 |
| 2-Acetylchlorin $e_6$ | Me | ACL | Me | Et | Me | $CO_2H$ | Ac | { H / Pr | { H / Me | 16,17 |
| 2-Formylchlorin $e_6$ | Me | CHO | Me | Et | Me | $CO_2H$ | Ac | { H / Pr | { H / Me | 16,17 |

Notes:
Me: —$CH_3$ (Methyl group)
Et: —$CH_2CH_3$ (Ethyl group)
Pr: —$CH_2CH_2COOH$ (Propionic acid group)
Ac: —$CH_2COOH$ (Acetic acid group)
V: —CH=$CH_2$ (Vinyl group)
ACL: $CH_3$—CO— (Acetyl group)

The amides used as the therapeutic agents according to the present invention are exemplified in the following. In the first place, the amides with amino monocarboxylic acids are exemplified.

Chlorin Derivatives (D,L)-Serinyl-trans-mesochlorin IX
Glycyl-trans-mesochlorin IX
α-(D,L)-Alanyl-trans-mesochlorin IX
β-Alanyl-trans-mesochlorin IX
εAmino-n-caproyl-mesochlorin IX
(D,L)-Serinyl chlorin $e_6$
(D,L)-Serinyl mesochlorin $e_6$
Glycyl chlorin $e_6$
Glycyl mesochlorin $e_6$
α-(D,L)-Alanyl chlorin $e_6$
α-(D,L)-Alanyl mesochlorin $e_6$
β-Alanyl chlorin $e_6$
β-Alanyl mesochlorin $e_6$
ε-Amino-n-caproyl chlorin $e_6$
ε-Amino-n-caproyl mesochlorin $e_6$ (D,L)-Serinyl chlorin $e_4$
(D,L)-Serinyl mesochlorin $e_4$
(D,L)-Serinyl isochlorin $e_4$
(D,L)-Serinyl mesoisochlorin $e_4$
Glycyl chlorin $e_4$
Glycyl mesochlorin $e_4$
Glycyl isochlorin $e_4$
Glycyl mesoisochlorin $e_4$
$\alpha$-(D,L)-Alanyl chlorin $e_4$
$\alpha$-(D,L)-Alanyl mesochlorin $e_4$
$\alpha$-(D,L)-Alanyl isochlorin $e_4$
$\alpha$-(D,L)-Alanyl mesoisochlorin $e_4$
$\beta$-Alanyl chlorin $e_4$
$\beta$-Alanyl mesochlorin $e_4$
$\beta$-Alanyl isochlorin $e_4$
$\beta$-Alanyl mesoisochlorin $e_4$
$\epsilon$-Amino-n-caproyl chlorin $e_4$
$\epsilon$-Amino-n-caproyl mesochlorin $e_4$
$\epsilon$-Amino-n-caproyl isochlorin $e_4$
$\epsilon$-Amino-n-caproyl mesoisochlorin $e_4$
(D,L)-Serinyl pyropheophorbide a
Glycyl pyropheophorbide a
$\alpha$-(D,L)-Alanyl pyropheophorbide a
$\beta$-Alanyl pyropheophorbide a
$\epsilon$-Amino-n-caproyl pyropheophorbide a
(D,L)-Serinyl pheophorbide a
Glycyl pheophorbide a
$\alpha$-(D,L)-Alanyl pheophorbide a
$\beta$-Alanyl pheophorbide a
$\epsilon$-Amino-n-caproyl pheophorbide a
(D,L)-Serinyl photoprotoporphyrin IX
Glycyl photoprotoporphyrin IX
$\alpha$-(D,L)-Alanyl-photoprotoporphyrin IX
$\beta$-Alanyl photoprotoporphyrin IX
$\epsilon$-Amino-n-caproyl photoprotoporphyrin IX
Threoninyl chlorin $e_6$
Tyrosyl chlorin $e_6$
Valyl chlorin $e_6$
Leucyl chlorin $e_6$
Isoleucyl chlorin $e_6$
Prolyl chlorin $e_6$
Methionyl chlorin $e_6$
Histidyl chlorin $e_6$
Arginyl chlorin $e_6$
Lysyl chlorin $e_6$
Glutaminyl chlorin $e_6$
4-Hydroxyprolyl chlorin $e_6$
5-Hydroxylysyl chlorin $e_6$
$\epsilon$-Amino-n-caproyl chlorin $e_6$
$\gamma$-Aminobutanoyl chlorin $e_6$
3-Methyl histidyl chlorin $e_6$
Alanyl-2-acetyl chlorin $e_6$
Valyl-2-acetyl chlorin $e_6$
Leucyl-2-acetyl chlorin $e_6$
Isoleucyl-2-acetyl chlorin $e_6$
Prolyl-2-acetyl chlorin $e_6$
Methionyl-2-acetyl chlorin $e_6$
Glycyl-2-acetyl chlorin $e_6$
Serinyl-2-acetyl chlorin $e_6$
Threoninyl-2-acetyl chlorin $e_6$
Cysteinyl-2-acetyl chlorin $e_6$
Tyrosyl-2-acetyl chlorin $e_6$
Asparginyl-2-acetyl chlorin $e_6$
Lysyl-2-acetyl chlorin $e_6$
Arginyl-2-acetyl chlorin $e_6$
Histidyl-2-acetyl chlorin $e_6$
Glutaminyl-2-acetyl chlorin $e_6$
4-Hydroxyprolyl-2-acetyl chlorin $e_6$
5-Hydroxylysyl-2-acetyl chlorin $e_6$
$\epsilon$-Amino-n-caproyl-2-acetyl chlorin $e_6$
$\gamma$-Aminobutanoyl-2-acetyl chlorin $e_6$
3-Methyl histidyl-2-acetyl chlorin $e_6$
$\beta$-Alanyl-2-formyl chlorin $e_6$
Valyl-2-formyl chlorin $e_6$
Leucyl-2-formyl chlorin $e_6$
Isoleucyl-2-formyl chlorin $e_6$
Prolyl-2-formyl chlorin $e_6$
Methionyl-2-formyl chlorin $e_6$
Glycyl-2-formyl chlorin $e_6$
Serinyl-2-formyl chlorin $e_6$
Threoninyl-2-formyl chlorin $e_6$
Cysteinyl-2-formyl chlorin $e_6$
Tyrosyl-2-formyl chlorin $e_6$
Asparginyl-2-formyl chlorin $e_6$
Lysyl-2-formyl chlorin $e_6$
Arginyl-2-formyl chlorin $e_6$
Histidyl-2-formyl chlorin $e_6$
Glutaminyl-2-formyl chlorin $e_6$
4-Hydroxyprolyl-2-formyl chlorin $e_6$
5-Hydroxylysyl-2-formyl chlorin $e_6$
$\epsilon$-Amino-n-caproyl-2-formyl chlorin $e_6$
$\gamma$-Aminobutanoyl-2-formyl chlorin $e_6$
3-Methyl histidyl-2-formyl chlorin $e_6$
$\beta$-Alanyl-2-formyl chlorin $e_6$
Alanyl deuterochlorin $e_6$
Valyl deuterochlorin $e_6$
Leucyl deuterochlorin $e_6$
Isoleucyl deuterochlorin $e_6$
Prolyl deuterochlorin $e_6$
Methionyl deuterochlorin $e_6$
Glycyl deuterochlorin $e_6$
Serinyl deuterochlorin $e_6$
Threoninyl deuterochlorin $e_6$
Cysteinyl deuterochlorin $e_6$
Tyrosyl deuterochlorin $e_6$
Asparginyl deuterochlorin $e_6$
Lysyl deuterochlorin $e_6$
Arginyl deuterochlorin $e_6$
Histidyl deuterochlorin $e_6$
Glutaminyl deuterochlorin $e_6$
4-Hydroxyprolyl deuterochlorin $e_6$
5-Hydroxylysyl deuterochlorin $e_6$
$\epsilon$-Amino-n-caproyl deuterochlorin $e_6$
$\gamma$-Aminobutanoyl deuterochlorin $e_6$
3-Methyl histidyl deuterochlorin $e_6$
$\beta$-Alanyl deuterochlorin $e_6$
Valyl mesochlorin $e_6$
Leucyl mesochlorin $e_6$
Isoleucyl mesochlorin $e_6$
Prolyl mesochlorin $e_6$
Methionyl mesochlorin $e_6$
Serinyl mesochlorin $e_6$ Threoninyl mesochlorin $e_6$
Cysteinyl mesochlorin $e_6$
Tyrosyl mesochlorin $e_6$
Asparginyl mesochlorin $e_6$
Lysyl mesochlorin $e_6$
Arginyl mesochlorin $e_6$
Histidyl mesochlorin $e_6$
Glutaminyl mesochlorin $e_6$
4-Hydroxyprolyl mesochlorin $e_6$
5-Hydroxylysyl mesochlorin $e_6$
$\gamma$-Aminobutanoyl mesochlorin $e_6$
3-Methyl histidyl mesochlorin $e_6$ Porphyrin Derivatives (D,L)-Serinyl mesoporphyrin IX
Glycyl mesoporphyrin IX
$\alpha$-(D,L)-Alanyl mesoporphyrin IX
$\beta$-Alanyl mesoporphyrin IX
$\epsilon$-Amino-n-caproyl mesoporphyrin IX
(D,L)-Serinyl protoporphyrin IX
Glycyl protoporphyrin IX
$\alpha$-(D,L)-Alanyl protoporphyrin IX
$\beta$-Alanyl protoporphyrin IX
$\epsilon$-Amino-n-caproyl protoporphyrin IX
(D,L)-Serinyl deuteroporphyrin IX
Glycyl deuteroporphyrin IX
$\alpha$-(D,L)-Alanyl deuteroporphyrin IX
$\beta$-Alanyl deuteroporphyrin IX
$\epsilon$-Amino-n-caproyl deuteroporphyrin IX
(D,L)-Serinyl coproporphyrin III
Glycyl coproporphyrin III
$\alpha$-(D,L)-Alanyl coproporphyrin III
$\beta$-Alanyl coproporphyrin III
$\epsilon$-Amino-n-caproyl coproporphyrin III
(D,L)-Serinyl hematoporphyrin IX
Glycyl hematoporphyrin IX
$\alpha$-(D,L)-Alanyl hematoporphyrin IX
$\beta$-Alanyl hematoporphyrin IX
$\epsilon$-Amino-n-caproyl hematoporphyrin IX Bacteriochlorin Derivatives (D,L)-Serinyl bacteriochlorin $e_4$
Glycyl bacteriochlorin $e_4$
$\alpha$-(D,L)-Alanyl bacteriochlorin $e_4$
$\beta$-Alanyl bacteriochlorin $e_4$
$\epsilon$-Amino-n-caproyl bacteriochlorin $e_4$
(D,L)-Serinyl bacterioisochlorin $e_4$
Glycyl bacterioisochlorin $e_4$
$\alpha$-(D,L)-Alanyl bacterioisochlorin $e_4$
$\beta$-Alanyl bacterioisochlorin $e_4$
$\epsilon$-Amino-n-caproyl bacterioisochlorin $e_4$
(D,L)-Serinyl bacteriochlorin $e_6$
Glycyl bacteriochlorin $e_6$
$\alpha$-(D,L)-Alanyl bacteriochlorin $e_6$
$\beta$-Alanyl bacteriochlorin $e_6$
$\epsilon$-Amino-n-caproyl bacteriochlorin $e_6$
(D,L)-Serinyl pyrobacteriopheophorbide a
Glycyl pyrobacteriopheophorbide a
$\alpha$-(D,L)-Alanyl pyrobacteriopheophorbide a
$\beta$-Alanyl pyrobacteriopheophorbide a
$\epsilon$-Amino-n-caproyl pyrobacteriopheophorbide a
(D,L)-Serinyl bacteriopheophorbide a
Glycyl bacteriopheophorbide a
$\alpha$-(D,L)-Alanyl bacteriopheophorbide a
$\beta$-Alanyl bacteriopheophorbide a
$\epsilon$-Amino-n-caproyl bacteriopheophorbide a In the following, di- or polyamides of amino monocarboxylic acids are further exemplified.

Chlorin Derivatives

Di-(D,L)-serinyl-trans-mesochlorin IX
Di-glycyl-trans-mesochlorin IX
Di-$\alpha$-(D,L)-alanyl-trans-mesochlorin IX
Di-$\beta$-alanyl-trans-mesochlorin IX
Di-$\epsilon$-amino-n-caproyl-mesochlorin IX
Di, tri-(D,L)-serinyl chlorin $e_6$
Di, tri-(D,L)-serinyl mesochlorin $e_6$
Di, tri-glycyl chlorin $e_6$
Di, tri-glycyl mesochlorin $e_6$
Di, tri-$\alpha$-(D,L)-alanyl chlorin $e_6$
Di, tri-$\alpha$-(D,L)-alanyl mesochlorin $e_6$
Di, tri-$\beta$-alanyl chlorin $e_6$
Di, tri-$\epsilon$-alanyl mesochlorin $e_6$
Di, tri-$\epsilon$-amino-n-caproyl chlorin $e_6$
Di, tri-$\epsilon$-amino-n-caproyl mesochlorin $e_6$
Di-(D,L)-serinyl chlorin $e_4$
Di-(D,L)-serinyl mesochlorin $e_4$
Di-(D,L)-serinyl isochlorin $e_4$
Di-(D,L)-serinyl mesoisochlorin $e_4$
Di-glycyl chlorin $e_4$
Di-glycyl mesochlorin $e_4$
Di-glycyl isochlorin $e_4$
Di-glycyl mesoisochlorin $e_4$
Di-$\alpha$-(D,L)-alanyl chlorin $e_4$
Di-$\alpha$-(D,L)-alanyl mesochlorin $e_4$
Di-$\alpha$-(D,L)-alanyl isochlorin $e_4$
Di-$\alpha$-(D,L)-alanyl mesoisochlorin $e_4$
Di-$\beta$-alanyl chlorin $e_4$
Di-$\beta$-alanyl mesochlorin $e_4$
Di-$\beta$-alanyl isochlorin $e_4$
Di-$\beta$-alanyl mesoisochlorin $e_4$
Di-$\epsilon$-amino-n-caproyl chlorin $e_4$
Di-$\epsilon$-amino-n-caproyl mesochlorin $e_4$
Di-$\epsilon$-amino-n-caproyl isochlorin $e_4$
Di-$\epsilon$-amino-n-caproyl mesoisochlorin $e_4$
Di-(D,L)-serinyl photoprotoporphyrin IX
Di-glycyl photoprotoporphyrin IX
Di-$\alpha$-(D,L)-alanyl-photoprotoporphyrin IX
Di-$\beta$-alanyl photoprotoporphyrin IX
Di-$\epsilon$-amino-n-caproyl photoprotoporphyrin IX Porphyrin Derivatives Di-(D,L)-serinyl mesoporphyrin IX
Di-glycyl mesoporphyrin IX
Di-$\alpha$-(D,L)-alanyl mesoporphyrin IX
Di-$\beta$-alanyl mesoporphyrin IX
Di-$\epsilon$-amino-n-caproyl mesoporphyrin IX
Di-(D,L)-serinyl protoporphyrin IX
Di-glycyl protoporphyrin IX
Di-$\alpha$-(D,L)-alanyl protoporphyrin IX
Di-$\beta$-alanyl protoporphyrin IX
Di-$\epsilon$-amino-n-caproyl protoporphyrin IX
Di-(D,L)-serinyl deuteroporphyrin IX
Di-glycyl deuteroporphyrin IX
Di-$\alpha$-(D,L)-alanyl deuteroporphyrin IX
Di-$\beta$-alanyl deuteroporphyrin IX
Di-$\epsilon$-amino-n-caproyl deuteroporphyrin IX
Di, tri, tetra-(D,L)-serinyl coproporphyrin III Di, tri, tetra-glycyl coproporphyrin III
Di, tri, tetra-α-(D,L)-alanyl coproporphyrin III
Di, tri, tetra-β-alanyl coproporphyrin III
Di, tri, tetra-β-amino-n-caproyl coproporphyrin III
Di-(D,L)-serinyl hematoporphyrin IX
Di-glycyl hematoporphyrin IX
Di-α-(D,L)-alanyl hematoporphyrin IX
Di-β-alanyl hematoporphyrin IX
Di-ε-amino-n-caproyl hematoporphyrin IX Bacteriochlorin Derivatives Di-(D,L)-serinyl bacteriochlorin $e_4$
Di-glycyl bacteriochlorin $e_4$
Di-α-(D,L)-alanyl bacteriochlorin $e_4$
Di-β-alanyl bacteriochlorin $e_4$
Di-ε-amino-n-caproyl bacteriochlorin $e_4$
Di-(D,L)-serinyl bacterioisochlorin $e_4$
Di-glycyl bacterioisochlorin $e_4$
Di-α-(D,L)-alanyl bacterioisochlorin $e_4$
Di-β-alanyl bacterioisochlorin $e_4$
Di-ε-amino-n-caproyl bacterioisochlorin $e_4$
Di, tri-(D,L)-serinyl bacteriochlorin $e_6$
Di, tri-glycyl bacteriochlorin $e_6$
Di, tri-α-(D,L)-alanyl bacteriochlorin $e_6$
Di, tri-β-alanyl bacteriochlorin $e_6$
Di, tri-ε-amino-n-caproyl bacteriochlorin $e_6$ Similarly, using other amino acids, the following peptides can be employed, however, they do not limit the present invention.
Di-threoninyl trans-mesochlorin IX
Di, tri-threoninyl chlorin $e_6$
Di, tri-threoninyl mesochlorin $e_6$
Di-threoninyl chlorin $e_4$
Di-threoninyl mesochlorin $e_4$
Di-threoninyl isochlorin $e_4$
Di-threoninyl mesoisochlorin $e_4$
Di-threoninyl photoprotoporphyrin IX
Di-threoninyl mesoporphyrin IX
Di-threoninyl protoporphyrin IX
Di-threoninyl deuteroporphyrin IX
Di, tri, tetra-threoninyl coproporphyrin III
Di-threoninyl hematoporphyrin IX
Di-threoninyl bacteriochlorin $e_4$
Di-threoninyl bacterioisochlorin $e_4$
Di, tri-threoninyl bacteriochlorin $e_6$
Di-cysteinyl trans-mesochlorin IX
Di, tri-cysteinyl chlorin $e_6$
Di, tri-cysteinyl mesochlorin $e_6$
Di-cysteinyl chlorin $e_4$
Di-cysteinyl mesochlorin $e_4$
Di-cysteinyl isochlorin $e_4$
Di-cysteinyl mesoisochlorin $e_4$
Di-cysteinyl photoprotoporphyrin IX
Di-cysteinyl mesoporphyrin IX
Di-cysteinyl protoporphyrin IX
Di-cysteinyl deuteroporphyrin IX
Di, tri, tetra-cysteinyl coproporphyrin III
Di-cysteinyl hematoporphyrin IX
Di-cysteinyl bacteriochlorin $e_4$
Di-cysteinyl bacterioisochlorin $e_4$
Di, tri-cysteinyl bacteriochlorin $e_6$
Di-tyrosyl trans-mesochlorin IX
Di, tri-tyrosyl chlorin $e_6$
Di, tri-tyrosyl mesochlorin $e_6$
Di-tyrosyl chlorin $e_4$
Di-tyrosyl mesochlorin $e_4$
Di-tyrosyl isochlorin $e_4$
Di-tyrosyl mesoisochlorin $e_4$
Di-tyrosyl photoprotoporphyrin IX
Di-tyrosyl mesoporphyrin IX
Di-tyrosyl protoporphyrin IX
Di-tyrosyl deuteroporphyrin IX
Di, tri, tetra-tyrosyl coproporphyrin III
Di-tyrosyl hematoporphyrin IX
Di-tyrosyl bacteriochlorin $e_4$
Di-tyrosyl bacterioisochlorin $e_4$
Di, tri-tyrosyl bacteriochlorin $e_6$
Di-valyl trans-mesochlorin IX
Di, tri-valyl chlorin $e_6$
Di, tri-valyl mesochlorin $e_6$
Di-valyl chlorin $e_4$
Di-valyl mesochlorin $e_4$
Di-valyl isochlorin $e_4$
Di-valyl mesoisochlorin $e_4$
Di-valyl photoprotoporphyrin IX
Di-valyl mesoporphyrin IX
Di-valyl protoporphyrin IX
Di-valyl deuteroporphyrin IX
Di, tri, tetra-valyl coproporphyrin III
Di-valyl hematoporphyrin IX
Di-valyl bacteriochlorin $e_4$
Di-valyl bacterioisochlorin $e_4$
Di, tri-valyl bacteriochlorin $e_6$
Di-leucyl trans-mesochlorin IX
Di, tri-leucyl chlorin $e_6$
Di, tri-leucyl mesochlorin $e_6$
Di-leucyl chlorin $e_4$
Di-leucyl mesochlorin $e_4$
Di-leucyl isochlorin $e_4$
Di-leucyl mesoisochlorin $e_4$
Di-leucyl photoprotoporphyrin IX
Di-leucyl mesoporphyrin IX
Di-leucyl protoporphyrin IX
Di-leucyl deuteroporphyrin IX
Di, tri, tetra-leucyl coproporphyrin III
Di-leucyl hematoporphyrin IX
Di-leucyl bacteriochlorin $e_4$
Di-leucyl bacterioisochlorin $e_4$
Di, tri-leucyl bacteriochlorin $e_6$
Di-isoleucyl trans-mesochlorin IX
Di, tri-isoleucyl chlorin $e_6$
Di, tri-isoleucyl mesochlorin $e_6$
Di-isoleucyl chlorin $e_4$
Di-isoleucyl mesochlorin $e_4$
Di-isoleucyl isochlorin $e_4$
Di-isoleucyl mesoisochlorin $e_4$
Di-isoleucyl photoprotoporphyrin IX
Di-isoleucyl mesoporphyrin IX
Di-isoleucyl protoporphyrin IX
Di-isoleucyl deuteroporphyrin IX
Di, tri, tetra-isoleucyl coproporphyrin III
Di-isoleucyl hematoporphyrin IX
Di-isoleucyl bacteriochlorin $e_4$
Di-isoleucyl bacterioisochlorin $e_4$
Di, tri-isoleucyl bacteriochlorin $e_6$
Di-prolyl trans-mesochlorin IX Di, tri-prolyl chlorin $e_6$
Di, tri-prolyl mesochlorin $e_6$
Di-prolyl chlorin $e_4$
Di-prolyl mesochlorin $e_4$
Di-prolyl isochlorin $e_4$
Di-prolyl mesoisochlorin $e_4$
Di-prolyl photoprotoporphyrin IX
Di-prolyl mesoporphyrin IX
Di-prolyl protoporphyrin IX
Di-prolyl deuteroporphyrin IX
Di, tri, tetra-prolyl coproporphyrin III
Di-prolyl hematoporphyrin IX
Di-prolyl bacteriochlorin $e_4$
Di-prolyl bacterioisochlorin $e_4$
Di, tri-prolyl bacteriochlorin $e_6$
Di-phenylalanyl trans-mesochlorin IX
Di, tri-phenylalanyl chlorin $e_6$
Di, tri-phenylalanyl mesochlorin $e_6$
Di-phenylalanyl chlorin $e_4$
Di-phenylalanyl mesochlorin $e_4$
Di-phenylalanyl isochlorin $e_4$
Di-phenylalanyl mesoisochlorin $e_4$
Di-phenylalanyl photoprotoporphyrin IX
Di-phenylalanyl mesoporphyrin IX
Di-phenylalanyl protoporphyrin IX
Di-phenylalanyl deuteroporphyrin IX
Di, tri, tetra-phenylalanyl coproporphyrin III
Di-phenylalanyl hematoporphyrin IX
Di-phenylalanyl bacteriochlorin $e_4$
Di-phenylalanyl bacterioisochlorin $e_4$
Di, tri-phenylalanyl bacteriochlorin $e_6$
Di-tryptophyl trans-mesochlorin IX
Di, tri-tryptophyl chlorin $e_6$
Di, tri-tryptophyl mesochlorin $e_6$
Di-tryptophyl chlorin $e_4$
Di-tryptophyl mesochlorin $e_4$
Di-tryptophyl isochlorin $e_4$
Di-tryptophyl mesoisochlorin $e_4$
Di-tryptophyl photoprotoporphyrin IX
Di-tryptophyl mesoporphyrin IX
Di-tryptophyl protoporphyrin IX
Di-tryptophyl deuteroporphyrin IX
Di, tri, tetra-tryptophyl coproporphyrin III
Di-tryptophyl hematoporphyrin IX
Di-tryptophyl bacteriochlorin $e_4$
Di-tryptophyl bacterioisochlorin $e_4$
Di, tri-tryptophyl bacteriochlorin $e_6$
Di-methionyl trans-mesochlorin IX
Di, tri-methionyl chlorin $e_6$
Di, tri-methionyl mesochlorin $e_6$
Di-methionyl chlorin $e_4$
Di-methionyl mesochlorin $e_4$
Di-methionyl isochlorin $e_4$
Di-methionyl mesoisochlorin $e_4$
Di-methionyl photoprotoporphyrin IX
Di-methionyl mesoporphyrin IX
Di-methionyl protoporphyrin IX
Di-methionyl deuteroporphyrin IX
Di, tri, tetra-methionyl coproporphyrin III
Di-methionyl hematoporphyrin IX
Di-methionyl bacterioohlorin $e_4$
Di-methionyl bacterioisochlorin $e_4$
Di, tri-methionyl bacteriochlorin $e_6$
Di-histidyl trans-mesochlorin IX
Di, tri-histidyl chlorin $e_6$
Di, tri-histidyl mesochlorin $e_6$
Di-histidyl chlorin $e_4$
Di-histidyl mesochlorin $e_4$
Di-histidyl isochlorin $e_4$
Di-histidyl mesoisochlorin $e_4$
Di-histidyl photoprotoporphyrin IX
Di-histidyl mesoporphyrin IX
Di-histidyl protoporphyrin IX
Di-histidyl deuteroporphyrin IX
Di, tri, tetra-histidyl coproporphyrin III
Di-histidyl hematoporphyrin IX
Di-histidyl bacteriochlorin $e_4$
Di-histidyl bacterioisochlorin $e_4$
Di, tri-histidyl bacteriochlorin $e_6$
Di-arginyl trans-mesochlorin IX
Di, tri-arginyl chlorin $e_6$
Di, tri-arginyl mesochlorin $e_6$
Di-arginyl chlorin $e_4$
Di-arginyl mesochlorin $e_4$
Di-arginyl isochlorin $e_4$
Di-arginyl mesoisochlorin $e_4$
Di-arginyl photoprotoporphyrin IX
Di-arginyl mesoporphyrin IX
Di-arginyl protoporphyrin IX
Di-arginyl deuteroporphyrin IX
Di, tri, tetra-arginyl coproporphyrin III
Di-arginyl hematoporphyrin IX
Di-arginyl bacteriochlorin $e_4$
Di-arginyl bacterioisochlorin $e_4$
Di, tri-arginyl bacteriochlorin $e_6$
Di-lysyl trans-mesochlorin IX
Di, tri-lysyl chlorin $e_6$
Di, tri-lysyl mesochlorin $e_6$
Di-lysyl chlorin $e_4$
Di-lysyl mesochlorin $e_4$
Di-lysyl isochlorin $e_4$
Di-lysyl mesoisochlorin $e_4$
Di-lysyl photoprotoporphyrin IX
Di-lysyl mesoporphyrin IX
Di-lysyl protoporphyrin IX
Di-lysyl deuteroporphyrin IX
Di, tri, tetra-lysyl coproporphyrin III
Di-lysyl hematoporphyrin IX
Di-lysyl bacteriochlorin $e_4$
Di-lysyl bacterioisochlorin $e_4$
Di, tri-lysyl bacteriochlorin $e_6$
Di-glutaminyl trans-mesochlorin IX
Di, tri-glutaminyl chlorin $e_6$
Di, tri-glutaminyl mesochlorin $e_6$
Di-glutaminyl chlorin $e_4$
Di-glutaminyl mesochlorin $e_4$
Di-glutaminyl isochlorin $e_4$
Di-glutaminyl mesoisochlorin $e_4$
Di-glutaminyl photoprotoporphyrin IX
Di-glutaminyl mesoporphyrin IX
Di-glutaminyl protoporphyrin IX
Di-glutaminyl deuteroporphyrin IX
Di, tri, tetra-glutaminyl coproporphyrin III
Di-glutaminyl hematoporphyrin IX
Di-glutaminyl bacteriochlorin $e_4$
Di-glutaminyl bacterioisochlorin $e_4$ Di, tri-glutaminyl bacteriochlorin $e_6$
Di-asparginyl trans-mesochlorin IX
Di, tri-asparginyl chlorin $e_6$
Di, tri-asparginyl mesochlorin $e_6$
Di-asparginyl chlorin $e_4$
Di-asparginyl mesochlorin $e_4$
Di-asparginyl isochlorin $e_4$
Di-asparginyl mesoisochlorin $e_4$
Di-asparginyl photoprotoporphyrin IX
Di-asparginyl mesoporphyrin IX
Di-asparginyl protoporphyrin IX
Di-asparginyl deuteroporphyrin IX
Di, tri, tetra-asparginyl coproporphyrin III
Di-asparginyl hematoporphyrin IX
Di-asparginyl bacteriochlorin $e_4$
Di-asparginyl bacterioisochlorin $e_4$
Di, tri-asparginyl bacteriochlorin $e_6$ In the following, mono-, di- or polyamides of amino dicarboxylic acids are exemplified.

Chlorin Derivatives

Mono and diaspartyl trans-mesochlorin IX
Mono and diglutamyl trans-mesochlorin IX
Mono, di and triaspartyl chlorin $e_6$
Mono, di and triaspartyl mesochlorin $e_6$
Mono, di and triglutamyl chlorin $e_6$
Mono, di and triglutamyl mesochlorin $e_6$
Mono and diaspartyl chlorin $e_4$
Mono and diaspartyl mesochlorin $e_4$
Mono and diaspartyl isochlorin $e_4$
Mono and diaspartyl mesoisochlorin $e_4$
Mono and diglutamyl chlorin $e_4$
Mono and diglutamyl mesochlorin $e_4$
Mono and diglutamyl isochlorin $e_4$
Mono and diglutamyl mesoisochlorin $e_4$
Monoaspartyl pyropheophorbide a
Monoglutamyl pyropheophorbide a
Monoaspartyl pheophorbide a
Monoglutamyl pheophorbide a
Mono and diaspartyl photoprotoporphyrin IX
Mono and diglutamyl photoprotoporphyrin IX
Mono and di-L-α-aminoadipyl trans-mesochlorin IX

Porphyrin Derivatives

Mono and diaspartyl mesoporphyrin IX
Mono and diglutamyl mesoporphyrin IX
Mono and diaspartyl protoporphyrin IX
Mono and diglutamyl protoporphyrin IX
Mono and diaspartyl deuteroporphyrin IX
Mono and diglutamyl deuteroporphyrin IX
Mono, di, tri and tetraaspartyl coproporphyrin III (isomer mixture)
Mono, di, tri and tetraglutamyl coproporphyrin III
Mono and diaspartyl hematoporphyrin IX
Mono and diglutamyl hematoporphyrin IX

Bacteriochlorin Derivatives

Mono and diaspartyl bacteriochlorin $e_4$
Mono and diglutamyl bacteriochlorin $e_4$
Mono and diaspartyl bacterioisochlorin $e_4$
Mono and diglutamyl bacterioisochlorin $e_4$
Mono, di and triaspartyl bacteriochlorin $e_6$
Mono, di and triglutamyl bacteriochlorin $e_6$
Monoaspartyl pyrobacteriopheophorbide a
Monoglutamyl pyrobacteriopheophorbide a
Monoaspartyl bacteriopheophorbide a
Monoglutamyl bacteriopheophorbide a The tetrapyrrole used in the present invention can be prepared by various synthetic methods which are found in the literatures. For example, the following literatures are exemplified with regard to chlorin e6.

(1) Willstatter, R. and Stoll, A.; *Investigations on Chlorophyll*, (Trans: Schertz, F. M., Merz, A. R.), p. 176, Science Printing Press, Lancaster, Pa., 1928.

(2) Willstatter, R. and Isler, M.; *Ann. Chem.*, 390, 269 (1912).

The compounds of the present invention are useful for the photodynamic therapy of atherosclerosis. When a man or animal, i.e., a mammal animal, having atherosclerosis is treated with doses of a compound of the present invention, the compound is accumulated selectively into the atherosclerotic lesion and when appropriate light rays of proper wavelength and intensity are applied, the compound emits fluorescence and produces cytotoxic singlet oxygen. Thereby the atherosclerotic lesion is cured by the cytotoxic singlet oxygen. The host of a living body to be dosed is a mammal having atherosclerosis in its body. The therapeutic agent of the present invention can be dosed to most animals, especially vertebrates, besides mammals having atherosclerosis, however, there is no necessity for it.

The compounds used for the photodynamic therapy should have the following properties:

(a) non-toxic at normal therapeutic dosage unless and until activated by light rays;

(b) should be accumulated selectively in atherosclerotic lesions;

(c) should be selectively photoactive on specific wavelengths;

(d) when irradiated with light rays or electromagnetic waves, they are activated to cytotoxic level in atherosclerotic lesion; and (e) easily metabolized or excreted after the treatment.

The foregoing compounds as the therapeutic agents of the present invention have the above properties and are also characterized by reasonable solubility in water at physiological pH.

As compared with the use of conventional tetrapyrroles such as hematoporphyrin derivatives and Photofrin II, the above-described compounds generate greater intensity of fluorescence in atherosclerotic lesions in which cholesterol is deposited to a similar degree with using the same quantities of doses. With the use of the compounds of the present invention, the atherosclerotic lesion provides more intense contrast to the normal tissue around the atherosclerotic lesion.

Furthermore, the intensity of fluorescence emitted from some of the conventionally used tetrapyrroles varies or the fluorescence emitted in the body of host varies from day to day, however, the intensity of fluorescence produced by the compounds of the present invention is quite stable.

The compounds of the present invention absorb activation energy for photodynamic therapy in the range of 300 to 800 nm, with the preferred compound absorbing in the 360 to 760 nm, i.e., light of longer wavelength which more readily permits penetration of energy into the atherosclerotic lesion for facilitating the purpose of photodynamic therapy.

Incidentally, the specific wavelength of fluorescence which is emitted from the compound of the present invention that is accumulated in the atherosclerotic lesion is shifted by about 10 nm as compared with that of the same compound in a phosphate buffered saline solution. From this fact, it is considered that the compound of the present invention is not physically caught simply within the atherosclerotic lesion but it is connected to the lesion by some interconnection mechanism. When the wavelength is shifted, the change in the intensity of fluorescence is also caused to occur usually. However, in the case of the compounds of the present invention, the intensity of fluorescence is not weakened but rather strengthened. Accordingly, the compounds of the present invention are most suitable for the photodynamic therapy.

According to the experience until now, the quantity of dosage can be reduced considerably because the compounds of the present invention are uniformly distributed all around the atherosclerotic lesion. Because the quantity of dose can be reduced, it is possible to suppress the occurrence of photodynamic sensitization in a host even when the administered compound is not excreted.

The quantity of administration of the compound of the present invention is determined depending on the degree of atherosclerotic lesion, wherein it is in the range of 0.01 to 100 mg/kg (weight of living body). The quantity is generally about 0.5 mg/kg. The compound of the present invention is apparently innocuous with the dose for the above-described therapeutic purpose. For example, no test animal was killed owing to the compound of the present invention in experiments using doses up to 20 mg/kg.

A compound of the present invention which is dissolved in an appropriate aqueous solution such as a phosphate buffered saline solution is administered by a proper method to the living body of a host to be treated. Besides the aqueous solution, it can be an aqueous dispersion containing a suitable dispersing agent. It is preferable that it is administered by a direct method such as intravenous injection. Meanwhile, the oral, intramuscular or hypodermic administration is also possible. In any case, the solution of the compound of the present invention may also contain the following known materials: a binder such as gum tragacanth; an excipient such as dicalcium phosphate; a disintegrating agent such as corn starch; a lubricant such as magnesium stearate; a sweetening agent such as sucrose; a preservative such as paraben; a dye; a flavoring such as cherry flavor; a solvent or dispersion medium such as water, ethanol or glycol; an antiseptic; and an isotonic agent such as sugar and sodium chloride.

These compounds can be prepared for use as preferable basic salts, for example sodium salts in the form of lyophilized pyrogen-free sterile compounds. The preferable type of therapeutic agent is (isotonic) solution used for injection.

Although the reason has not been clear, the compounds of the present invention are specifically and selectively accumulated in the atherosclerotic lesion in a living body. Accordingly, after the passage of a proper time, for example, in several minutes to several tens of hours after the administration into a vein, light rays are applied to the atherosclerotic lesion.

The light source for the irradiation in treatment is not limited, however, a laser beam is generally used because an intense light ray within a desired wavelength range can be applied selectively. Usable sources for the irradiation of laser beams are a strong continuous light source through a filter, exited dye laser or other laser apparatus, and transmitted beam system. As described above, the wavelength of the laser beam is in the range of 360 to 760 nm, for example 664 nm. The intensity of irradiation is appropriately selected generally from the range of 10 to 1000 mW/cm$^2$, preferably 20 to 500 mW/cm$^2$ and. The capacity of the laser apparatus is at least 500 mW. Some of commercially available laser apparatus meets these requirements.

In the practice of photodynamic therapy, the laser beam irradiation is carried out from the tip end of quartz fiber bundle after administering the compound. This can be done by contacting the tip end of quartz fiber bundle with the atherosclerotic lesion as well as by applying the tip end to the surface of atherosclerotic lesion from a working distance of about 5 mm. The irradiated state is observed directly by naked eyes or with an image on a CRT screen.

Concerning the treatment with the compound of the present invention, two approaches were proposed by the present inventors. One method is to treat by a intravascular catheterization and the other method is to treat on the outside of an adventitia of the artery (laparoscopic approach).

In the former treating method by intravascular catheterization, the specific fluorescence is observed by applying a laser beam directly to the inside wall of the artery to determine correctly atherosclerotic lesions, so that direct (accurate and local) treatment can be done.

In the latter treating method, a laser beam is applied to the outside of the adventitia of artery without inserting the catheter into artery and specific fluorescence is observed from the outside of the artery to determine the location of atherosclerotic lesion, however, it is possible to treat the atherosclerotic lesion directly like the former method. This therapeutic method on the outside of adventitia of artery can be employed in the treatment of coronary arteries, arteries of lower limbs, cerebral arteries and cerebral infarction where the inspection with an angiro-scopic catheter into artery is impossible.

In the following, the present invention is described in more detail with examples of medical effect tests concerning the compounds of the present invention.

Photodynamic therapy was carried out by administering the compounds of the present invention to hypercholesterolemia rabbits having atherosclerotic lesions which closely resemble the human atherosclerosis in morphological and biochemical characteristics.

The following two kinds of compounds were used for the tests:

Mono-L-aspartyl chlorin e$_6$ (hereinafter referred to as "NPe$_6$")

Mono-L-serinyl chlorin e$_6$ (hereinafter referred to as "MSe$_6$").

As a control, Photofrin II (trademark, made by Photofrin Medica Inc.) was used. These compounds were used by dissolving in phosphate buffer solution (pH 7.4).

PREPARATION EXAMPLE 1

Preparation of Mono-L-Aspartyl Chlorin e$_6$

Chlorin e$_6$ (as a free acid) was prepared according to the procedure of Fischer and Stern, Di Chemie Des Pyrroles, Volume II, second half, Leipzig 1940, Akademische Verlagsgesellschaft, pp. 91-93.

150 mg of chlorin e$_6$ and 250 mg of L-aspartic acid i-tert-butyl ester hydrochloride were dissolved in 20 ml of dimethyl formamide. There was made a total of 3-100 mg additions of N,N'-dicyclohexylcarbodiimide at one hour intervals. After 4 hours, the reaction mixture was diluted with 300 ml ether, washed twice with 200 ml H$_2$O, then extracted with 40 ml 1M KOH. The KOH solution was allowed to hydrolyze overnight, then heated to 70° C. for 10 minutes.

The pH of the solution was adjusted to 7, then any residual ether was removed by flash evaporation. The solution was then applied to a reverse phase (C-18 silica) column (1.5 cm $\phi \times 30$ cm). The product was purified by a stepwise elution of methanol/0.01M KPO$_4$ buffer (pH 6.85). Eluted with 5% methanol until unwanted polar pigments were removed. Monoaspartyl chlorin e$_6$ was eluted off with 6–8% methanol, and unreacted chlorin e$_6$ was removed with 25% methanol.

The product was precipitated at pH 3 after flash evaporating briefly to remove methanol, then washed by the centrifuge 3 times with dilute acetic acid.

The product was dried under vacuum. Yield of mono-L-aspartyl chlorin e$_6$ was 50 mg.

PREPARATION EXAMPLE 2

Preparation of Mono-L-Serinyl chlorin e$_6$

Chlorin e$_6$ prepared in the like manner as in Preparation Example 1 was used. 100 mg of the chlorine e$_6$ and 35 mg of 1-ethyl-3-(3-dimethylaminopropyl)carbodiimide hydrochloride were dissolved in 2 ml of N,N'-dimethyl formamide. After 5 minutes, 125 mg of L-serine benzyl ester hydrochloride was added, stirred vigorously until solution was complete, then allowed to stand at room temperature for 2 hours. At this time, 0.5 ml of glacial acetic acid was added, then 30 ml of methanol and 12 ml of H$_2$O.

The solution was applied to a C-18 reverse phase column. The column was washed with H$_2$O (100 ml) then 4 ml of 1M NH$_4$OH, then H$_2$O again (50 ml). Eluted the product with MeOH/H$_2$O. Fractions eluted from the column with 30% to 80% MeOH contained product as well as carbodiimide-activated chlorin as determined by TLC on C-18 reverse phase plates with solvent 70% MeOH/30% buffer (0.1M sodium phosphate pH 6.85) V/V.

These fractions were pooled and enough 3N NaOH was added to make the solution 0.1N in NaOH. After 1 hour, the hydrolysis was complete as determined by TLC in the above system. Removed the methanol by rotary evaporation and adjusted the pH of the solution to 7.5 with HCl. The chlorin solution was then reapplied to the same reverse phase column, washed with water, and eluted with MeOH/water using a stepwise gradient solution from 10 to 50% methanol. The fractions containing pure mono-L-serinyl chlorin as determined by TLC (R$_f$ slightly greater than the unsubstituted chlorin) were pooled, the methanol was removed by rotary evaporation, and the product was dried as the trisodium salt by lyophilization.

Animal Test

Normal New Zealand white rabbits (supplied by Japan Laboratory Animals Inc.) which took artificial atherosclerosis (hereinafter referred to as "atherosclerotic rabbits") were used for experiments. These rabbits are suitable for the tests of this kind because they correspond well to the diseases of mankind.

The white rabbits were fed on an atherogenic diet containing 0.5% cholesterol and 10% peanut oil for 12 to 20 weeks, thereby obtaining atherosclerotic rabbits of 4 kg weight. Three rabbits were used for a group of therapeutic test with each treating agent. The used rabbits were affected by the disease of the same degree.

Test Apparatus

The apparatus for this experiment includes a catheter of 2.1 mm in diameter (made by Sumitomo Electric Industries, Ltd.), an argon dye laser (made by Spectrum Physics) for exciting photosensitive substance and a fluorescence analyzer system. The wavelengths of the argon dye laser for exciting photosensitive substance can be adjusted to 405 nm, 630 nm and 664 nm corresponding to the absorption bands of respective substances and it was used at an output of 100 mW/cm$^2$. This laser beam was introduced into a quartz fiber bundle of 300 micrometer in core diameter and it was then passed into an artery in Treatment Example 1. A laser beam fiber bundle was hand-held and directed along the outside of adventitia of the artery from a working distance of 5 mm in Treatment Example 2.

TREATMENT EXAMPLE 1

In Table 3, the treatment method with intravascular catheterization is shown.

TABLE 3

| Treatment with Intravascular Catheterization | | | | | |
|---|---|---|---|---|---|
| Compound | Dose mg/kg | Time(*) hrs | Wavelength nm | Intensity mW/cm$^2$ | Power J/cm$^2$ |
| Photofrin II | 0.5 | 6 | 405 | 100 | 50 |
| NPe$_6$ | 0.5 | 6 | 405 | 100 | 50 |
| NPe$_6$ | 0.5 | 6 | 664 | 100 | 50 |
| MSe$_6$ | 0.5 | 6 | 405 | 100 | 50 |

(*)Time length from dosage to irradiation

According to Table 3, a photosensitive substance of 0.5 mg/1 kg was administered to atherosclerotic rabbits of 4 kg in weight from the veins of their ears. Six hours after the administration, a catheter was inserted by about 30 cm through the femoral artery by cutdown under the anesthesia with Nembutal sodium solution. The fluorescence photosensitive substance which was accumulated in the atherosclerotic lesion was measured by scanning the intima of the artery with the beam of an argon dye laser. The treatment was then carried out by directly applying a laser beam with total energy of 50 J/cm$^2$ to the atherosclerotic lesion in the aortic arch, in which it was observed that a sufficient quantity of the photosensitive substance was accumulated. After the treatment, the abdomen was closed and an antibiotic was injected in the wound and abdominal cavity and rabbits were bred for 1 week with normal feed.

TREATMENT EXAMPLE 2

In Table 4, the treatment with laparoscopic approach is shown.

TABLE 4

| Treatment with Laparoscopic Approach | | | | | |
|---|---|---|---|---|---|
| Compound | Dose mg/kg | Time(*) hrs | Wavelength nm | Intensity mW/cm$^2$ | Power J/cm$^2$ |
| Photofrin II | 0.5 | 6 | 630 | 100 | 50 |
| NPe$_6$ | 0.5 | 6 | 664 | 100 | 50 |
| NPe$_6$ | 0.5 | 6 | 405 | 100 | 50 |
| MSe$_6$ | 0.5 | 6 | 664 | 100 | 50 |

(*)Time length from dosage to irradiation

According to Table 4, a photosensitive substance of 0.5 mg/1 kg was administered to atherosclerotic rabbits of 4 kg in weight from the veins of their ears. Six hours after the administration, the abdominal aorta was exposed through sterile laparotomy with the anesthesia. A laser beam through a catheter was applied to the outside of adventitia of artery to excite the photosensitive substance which was accumulated in the atherosclerotic lesion. The treatment was then carried out by directly applying a laser beam with total energy of 50 J/cm$^2$ to the outside of the of branchial artery in which it was observed that a sufficient quantity of the photosensitive substance was accumulated. After the treatment, the abdomen was closed and an antibiotic was injected in the wound and abdominal cavity and rabbits were bred for 1 week with normal feed.

Evaluation of Therapeutic Effect (1) Determination of Atherosclerotic Lesion by Photodynamic Diagnosis In order to confirm the treated portion of the atherosclerotic lesion, the same compound was administered in 0.5 mg/1 kg to the treated part of each rabbit from the veins of the ear. Six hours after the administration, the rabbits were subjected to laparotomy under the anesthesia with Nembutal sodium solution. The outer side of the treated area was irradiated with a laser beam of 405 nm in wavelength (100 mW/cm$^2$) to excite the photosensitive substance which accumulated in the intima of artery and the generated fluorescence was measured from the outside of the artery. The quantity of accumulated photosensitive substance was estimated by calculating the intensity of fluorescence with the integrated area on fluorescent spectrum within the range of 600 to 700 nm, which were measured in several parts of arterial walls. The quantity of compound accumulated in the atherosclerotic lesion has correlation with the degree of the athero-sclerosis. Accordingly, it is possible to determine the degree of seriousness in the atherosclerosis by comparing the accumulated quantities.

(2) Ocular and Histological Diagnosis

After the above test (1), animals were scrificed with anesthesia and aorta was excised and specimens were serially sectioned, with which histological diagnosis was carried out by staining them with hematoxylin-eosin dye and Sudan III fat dye.

(3) Comparative Observation of Fluorescences and Histological Types of Photosensitive Substances Using Fluorescence Microscope Some of the serial specimens prepared in the above test (2) were instantly stored in a cooled dark room as the specimens for the fluorescence microscope observation. Within 1 hour after the preparation of the specimens, the distribution of respective photosensitive substances in vessel structures and histological types were comparatively observed in the dark room with a fluorescence microscope.

Test Result 1

The results of treatment in Treatment Example 1 with intravascular catheterization are described in the following.

Each rabbit was administered with a photosensitive substance and the atherosclerotic lesion in the aortic arch was treated with intravascular catheterization. After 1 week, the same compound was administered to perform photodynamic diagnosis to determine the intensity of fluorescence of the photosensitive substance accumulated in the intima from the outside of the aorta, which was compared with the intensity of fluorescence before the treatment (cf. Table 5). As a result, the intensities of fluorescence of Photofrin II Group in the atherosclerotic lesion of the arch were 5.1 before the treatment and 3.3 after the treatment. In the case of NPe$_6$, the intensities of fluorescence were 21.0 before the treatment and 3.6 after the treatment. In the case of MSe$_6$, the intensities of fluorescence were 19.2 before the treatment and 3.4 after the treatment. In Photofrin II Group, the ratio of fluorescence intensity after the treatment to that before the treatment was about 65%, however, in NPe$_6$ and MSe$_6$ Groups, the corresponding values were as low as about 17%. Therefore, it was understood that the degree of atherosclerosis is much reduced in the cases of NPe$_6$ and MSe$_6$ Groups as compared with the case of Photofrin II.

TABLE 5

Fluorescence Intensities before and after Treatment with Intravascular Catheterization in Atherosclerotic Lesions

| Compound | Wavelength | Fluorescence Intensity of Photosensitive Substance | |
|---|---|---|---|
| | | Before Treatment | After Treatment |
| Photofrin II | 405 nm | 5.1 | 3.3 |
| NPe$_6$ | 405 nm | 21.0 | 3.6 |
| NPe$_6$ | 664 nm | 19.0 | 3.0 |
| MSe$_6$ | 405 nm | 19.2 | 3.4 |
| No Dosage | 405 nm | 0.0 | 0.0 |

Shown in Table 6 are the results of histological diagnosis with preparing serial specimens of the same parts of the aortic arch. In the Group of No Dosage, the observed atherosclerotic layer between the intima and media of arterial wall contained dense cells with fat particles which could be stained intensely by Sudan III fat staining (+5). It was ocularly observed that intimal thickness was spread in the entirety and the arterial wall was very hard (+5). In the aortic arch of Photofrin Group, the lowering of hardness was slightly recognized (+3) as compared with the case of No Dosage Group and the Sudan III fat staining in the atherosclerotic layer was also lowered to some extent (+3). However, the difference was not so significant as compared with the degree of atherosclerosis of No Dosage Group and no marked therapeutic effect could be obtained.

On the other hand, in the aortic arch of NPe$_6$ Group, the intimal thickness were reduced, the arterial wall was thin and the hardness was low (±0 to +1) as compared with No Dosage Group. Furthermore, in the histological diagnosis, the Sudan III fat staining property of the atherosclerotic layer between the intima and media of the arterial wall was lowered and the exfoliation of atherosclerotic lesion with causing vacuolation was histologically conspicuous (+1).

The treatment with NPe$_6$ applying laser beams of two kinds of absorption bands of 405 nm and 664 nm gave similar high therapeutic effects.

The results of observation of aortic arch in MSe$_6$ Group were almost the same as those of NPe$_6$ Group.

As described above, the therapeutic effects of NPe$_6$ Group and MSe$_6$ Group were high as compared with the effect of Photofrin II Group and the alleviation of atherosclerosis and improvement in the lesions was markedly observed.

TABLE 6

Test Results in the Parts Treated

TABLE 6-continued

| | | with Intravascular Catheterization | | |
|---|---|---|---|---|
| Compound | Wavelength | (1) Histological Diagnosis Stainability with Sudan III | (2) Palpation Elasticity Extensibility | (3) Ocular Diagnosis Degree of Atherosclerosis |
| Photofrin II | 405 nm | +3 | +3 | +3 |
| NPe6 | 405 nm | ±0 | ±0 | +1 |
| NPe6 | 664 nm | ±0 | ±0 | +1 |
| MSe6 | 405 nm | ±0 | ±0 | +1 |
| No Dosage | 405 nm | +5 | +5 | +5 |

Evaluation:
(1) Histological Diagnosis: State of atherosclerotic layer and fat stainability with Sudan III
Evaluation: ±0 → +5

| Artery was not fat-stained, close to normal artery | → | Atherosclerotic layer was stained to reddish brown uniformly |

(2) Palpation: Degrees of elasticity and extensibility
Evaluation: ±0 → +5

| Elasticity and extensibility were like normal artery | → | Hardened state without elasticity |

(3) Ocular Diagnosis: The degree of atherosclerosis in view of the occurrence of white intimal thickness
Evaluation: ±0 → +5

| Color and state of arterial intima were like normal artery | → | Much white intimal thickness formed |

Test Result 2

The results in Treatment Example 2 treated with the laparoscopic approach are described in the following.

Each rabbit was administered with a photosensitive substance and treated on the outside of the adventitia of branchial artery. After 1 week, the same compound was administered to perform photodynamic diagnosis to determine the intensity of fluorescence of the photosensitive substance accumulated in the intima from the outside of the adventitia of artery. Furthermore, serial specimens of the same part were prepared and histological inspection was carried out (Tables 7, 8 and 9).

According to these results, the intensity of fluorescence in Photofrin II Group (Table 7) was about 4.5 in the periphery of treated area and about 2.8 in the treated area, which indicated that the accumulation of Photofrin II was not significantly different in these areas. In the cases of NPe6 Group (Table 8) and MSe6 (Table 9), the intensity of fluorescence was as high as 16 to 20 in the periphery of treated area and as low as 2 to 3 in the treated area, which indicated that the accumulated quantities in the treated areas were reduced to about one-fifth and the atherosclerosis was lightened.

Serial specimens of the same part were prepared in the above NP6 Group and they were observed with fluorescence microscope, in which it was understood that the strong fluorescence in the periphery of treated area was emitted from the atherosclerotic layer between the intima and media of arterial wall and the fluorescence was not observed in the adventitia and elastic fibers of normal tissue. Furthermore, the fluorescence of NPe6 was hardly observed in atherosclerotic layer between the intima and media in the treated area.

In the ocular and histological inspection on Photofrin II Group, the hardness in the treated area was slightly lowered (+3) as compared with that of the peripheral area and the Sudan III fat staining property of the atherosclerotic layer was a little lowered (+3 to +4), however, no significant difference in the degree of atherosclerosis could be found and marked therapeutic effect could not be obtained.

Meanwhile, in the periphery of treated areas of NPe6 Group and MSe6 Group, white intimal thickness were apparently generated (+5) and the atherosclerotic layers which were strongly susceptible to Sudan III fat staining were confirmed (+5). Meanwhile, in the treated area, the intimal thickness were reduced (+1) and the arterial walls became thin to some extent, and according to histological inspection, the Sudan III fat staining of atherosclerotic layer between intima and media of arterial wall was lowered and the exfoliation of atherosclerotic lesion with causing vacuolation was histologically conspicuous (±1).

The treatment with NPe6 applying laser beams of two kinds of absorption bands of 405 nm and 664 nm gave similar high therapeutic effects like Treatment Example 1.

As described above, the therapeutic effects of NPe6 and MSe6 Groups were higher than the effect of Photofrin II Group and the alleviation of atherosclerosis and the improvement in the atherosclerotic lesions were markedly recognized.

TABLE 7

Test Results of Treatment with Laparoscopic Approach (Administration of Photofrin II)

| | Measured Point | Photodynamic Diagnosis Intensity of Fluorescence | Histological Diagnosis Stainability with Sudan III | Palpation Elasticity Extensibility | Ocular Diagnosis Degree of Atherosclerosis |
|---|---|---|---|---|---|
| 1 | −1.5 cm | 4.5 | +5 | +4 | +5 |
| 2 | −1.0 cm | 4.2 | +5 | +4 | +5 |
| 3 | Treated Area | 3.0 | +3 | +3 | +3 |
| 4 | Treated Area | 2.6 | +4 | +3 | +3 |
| 5 | +1.0 cm | 4.4 | +5 | +5 | +5 |
| 6 | +1.5 cm | 4.7 | +5 | +5 | +5 |

TABLE 8

Test Results of Treatment with Laparoscopic Approach (Administration of NPe6)

| | Measured Point | Photodynamic Diagnosis Intensity of Fluorescence | Histological Diagnosis Stainability with Sudan III | Palpation Elasticity Extensibility | Ocular Diagnosis Degree of Atherosclerosis |
|---|---|---|---|---|---|
| 1 | −1.5 cm | 19.8 | +5 | +4 | +5 |
| 2 | −1.0 cm | 19.2 | +5 | +4 | +5 |
| 3 | Treated Area | 2.7 | ±0 | +1 | +1 |
| 4 | Treated Area | 2.5 | ±0 | +1 | +1 |
| 5 | +1.0 cm | 18.3 | +5 | +5 | +5 |
| 6 | +1.5 cm | 20.3 | +5 | +5 | +5 |

TABLE 9

Test Results of Treatment with Laparoscopic Approach (Administration of MSe₆)

| Measured Point | | Photo-dynamic Diagnosis Intensity of Fluorescence | Histological Diagnosis Stainability with Sudan III | Palpation Elasticity Extensibility | Ocular Diagnosis Degree of Atherosclerosis |
|---|---|---|---|---|---|
| 1 | −1.5 cm | 18.0 | +5 | +4 | +5 |
| 2 | −1.0 cm | 17.1 | +5 | +4 | +5 |
| 3 | Treated Area | 3.0 | ±0 | +1 | +1 |
| 4 | Treated Area | 2.7 | ±0 | +1 | +1 |
| 5 | +1.0 cm | 16.0 | +5 | +5 | +5 |
| 6 | +1.5 cm | 17.5 | +5 | +5 | +5 |

Concerning the above compounds, the test of acute toxicity among toxicological properties was carried out.

NPe₆ was intravenously administered to mice (strain C3H/HEJ) to determine the 50% lethal dose (LD₅₀) The value of LD₅₀ in male was 214 mg/kg and 187 mg/kg in female.

DISCUSSION (1) The photodynamic therapy with NPe₆ and MSe₆ is effective for regression of atherosclerosis and curing lesion. In comparison with the treatment with Photofrin II, higher therapeutic effect (regression of atherosclerotic lesion) can be expected when the same quantities of treating agents are administered to the atherosclerotic disease on the same degree.

(2) In the photodynamic diagnosis with NPe₆ and MSe₆, more excellent selective accumulation in the atherosclerotic lesion in comparison with Photofrin was confirmed. Even a small dose of the compound can identify the atherosclerotic lesion, thereby enabling to concentrate the treatment of disease only to atherosclerotic lesions.

(3) In the use of NPe₆, the treatment with laser beams of either 405 nm or 664 nm in wavelength corresponding to its absorption bands, can provide high therapeutic effects.

(4) The foregoing compounds can produce high therapeutic effects in any of the two newly elaborated methods of the present invention of the intravascular catheterization therapy and the laparoscopic approach.

The latter treatment with irradiation to adventitia of artery can be employed in the treatment of coronary arteries, arteries of lower limbs, cerebral arteries and cerebral infarction where the catheterizing into the artery is impossible.

The compound of the present invention was administered to serious atherosclerotic rabbits for photodynamic therapy and the following effects were obtained:

(1) The disease can be treated directly and exactly because the compound is selectively accumulated into the atherosclerotic lesion.

(2) The hardness of atherosclerotic lesion is lowered, the intimal thickness is regressed and exfoliation of fat cells is observed one week after the treatment.

(3) In comparison with the conventionally used Photofrin II or the like, more distinct therapeutic effect can be obtained when the same quantity is used for atherosclerotic lesion of the same degree of seriousness.

What is claimed is:

1. A method for treating atherosclerosis in mammals which comprises administering to a mammal an atherosclerosis-inhibiting effective amount of a fluorescent tetrapyrrole compound that accumulates in an atherosclerotic lesion within said mammal and applying light of sufficient wavelength and intensity to produce a cytotoxic effect on said atherosclerotic lesion, wherein said compound is of the formula:

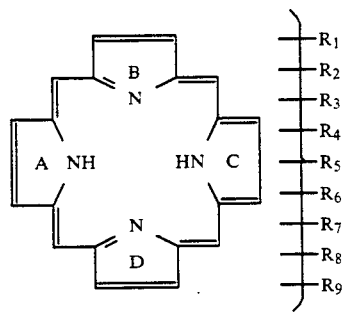

or a corresponding dihydrotetrapyrrole or tetrahydropyrrole carboxylic acid; or corresponding monoamides, diamides and polyamides of said tetrapyrrole carboxylic acid with an aminomonocarboxylic acid or a dicarboxylic acid; or pharmacologically acceptable salts thereof; wherein:

$R_1$ is methyl,

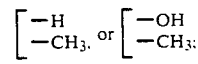

$R_2$ is H, vinyl, ethyl, —CH(OH)—CH₃, acetyl,

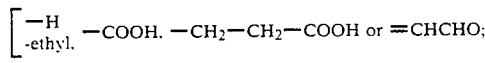

$R_3$ is methyl,

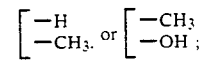

$R_4$ is H, vinyl, ethyl, —CH(OH)—CH₃, —CH₂—CH₂—COOH, =CHCHO, or

$R_5$ is methyl;
$R_6$ is H, —CH₂—CH₂—COOH, —CH₂—CH₂—COOR or COOH;
$R_7$ is —CH₂—CH₂—COOH, —CH₂—CH₂—COOR or

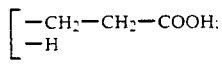

$R_8$ is m ethyl or

$R_9$ is H, —COOH, —CH$_2$—COOH or methyl; provided that when $R_1$, $R_2$, $R_3$, $R_4$, $R_7$ and $R_8$ are each two substituents or when $R_1$, $R_2$, $R_3$, $R_7$ and $R_8$ are divalent and attached to the same carbon, the pyrrole ring is a dihydropyrrole;

R is a lower alkyl or benzyl;

$R_6$ and $R_9$ when taken together are —CO—CH$_2$— or

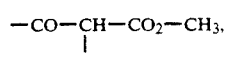

with the proviso that at least one of $R_1$ to $R_9$ is a free carboxyl group.

2. The method of claim 1 wherein said wavelength is about 300 nm to about 800 nm.

3. The method of claim 1 wherein said wavelength is about 360 nm to about 664 nm.

4. The method of claim 1 wherein said intensity is about 10 mW/cm$^2$ to about 1000 mW/cm$^2$.

5. The method of claim 1 wherein said intensity is about 20 mW/cm$^2$ to about 500 mW/cm$^2$.

6. The method of claim 1 wherein said aminomonocarboxylic acid or said dicarboxylic acid of said amide is a natural α-amino-monocarboxylic acid or a natural dicarboxylic acid.

7. The method of claim 1 wherein said tetrapyrrole has at least three carboxylic acids.

8. The method of claim 1 wherein said aminomonocarboxylic acid is serine, glycine, α-aminoalanine, β-aminoalanine, ε-amino-n-caproic acid, piperidine-2-carboxylic acid, piperidine-6-carboxylic acid, pyrrole-2-carboxylic acid, piperidine-6-propionic acid or pyrrole-5-acetic acid.

9. The method of claim 1 wherein said amino dicarboxylic acid is α-aminosuccinic acid, α-aminoglutaric acid, β-aminoglutaric acid, β-aminosebacic acid, 2,6-piperidine dicarboxylic acid, 2,5-pyrrole dicarboxylic acid, 2-carboxypyrrole-5-acetic acid, 2-carboxypiperidine-6-propionic acid, α-aminoadipic acid or α-aminoazelaic acid.

10. The method of claim 1 wherein said tetrapyrrole is coproporphyrin III, deuteroporphyrin IX, hematoporphyrin IX, protoporphyrin IX, photoprotoporphyrin IX, mesoporphyrin IX, transmesochlorin IX, trans-mesochlorin IX, chlorin e$_4$, chlorin e$_6$, mesochlorin e$_4$, isochlorin e$_4$, mesoisochlorin e$_4$, mesochlorin e$_6$, bacteriochlorin e$_6$, bacteriochlorin e$_4$, bacterioisochlorin e$_4$, 2-desvinylchlorin e$_6$, deuterochlorin e$_6$, 2-acetylchlorin e$_6$ or 2-formylchlorin e$_6$.

11. The method of claim 1 wherein said tetrapyrrole is:

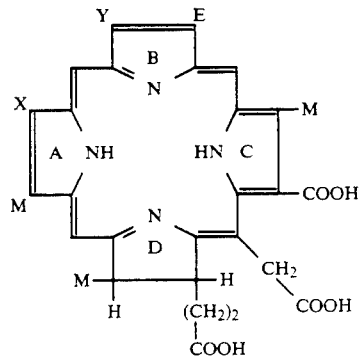

and wherein:

X is H, vinyl, ethyl, acetyl or formyl;
Y is methyl or formyl;
M is methyl; and
E is ethyl.

12. The method of claim 1 wherein said tetrapyrrole is chlorin or chlorin e$_6$.

13. The method of claim 1 wherein said tetrapyrrole is chlorin e$_6$.

* * * * *

UNITED STATES PATENT AND TRADEMARK OFFICE
CERTIFICATE OF CORRECTION

PATENT NO. : 5,308,861
DATED : May 3, 1994
INVENTOR(S) : Katsuo Aizawa, et al.

It is certified that error appears in the above-indentified patent and that said Letters Patent is hereby corrected as shown below:

Column 5, line 64: "(D.L)" should read --(D,L)--

Column 5, line 68: "$\epsilon$ Amino" should read --$\epsilon$-Amino--

Column 8, line 11: "$\beta$-Alanyl-2-formyl" should read --$\beta$-Alanyl-2-acetyl--

Column 8, line 12, insert the following: --Alanyl-2-formyl chlorin $e_6$--

Column 10, line 19: "Di, tri-$\epsilon$-alanyl" should read --Di, tri-$\beta$-alanyl--

Column 11, line 4: "tetra-$\beta$-amino" should read --tetra-$\epsilon$-amino--

Column 13, line 63: "bacterioohlorin" should read --bacteriochlorin--

UNITED STATES PATENT AND TRADEMARK OFFICE
CERTIFICATE OF CORRECTION

PATENT NO. : 5,308,861
DATED : May 3, 1994
INVENTOR(S) : Katsuo Aizawa, et al.

It is certified that error appears in the above-indentified patent and that said Letters Patent is hereby corrected as shown below:

Column 18, line 67: "i-tert" should read --di-tert--

Column 21, line 8: delete second occurrence of --of--

Column 22, line 4: before "arch" insert --aortic--

Column 27, line 8, Claim 1: after "$R_3$," insert --$R_4$,--

Signed and Sealed this

Twenty-eight Day of February, 1995

Attest:

BRUCE LEHMAN

Attesting Officer

Commissioner of Patents and Trademarks